United States Patent [19]

Johnson et al.

[11] Patent Number: 5,498,608
[45] Date of Patent: Mar. 12, 1996

[54] USE OF 2-HYDROXY-5-PHENYLAZOBENZOIC ACID DERIVATIVES AS COLON CANCER CHEMOPREVENTATIVE AND CHEMOTHERAPEUTIC AGENTS

[75] Inventors: Lorin K. Johnson, Pleasanton; Marvin H. Sleisenger, Kentfield, both of Calif.

[73] Assignee: Salix Pharmaceuticals, Palo Alto, Calif.

[21] Appl. No.: 178,578

[22] Filed: Jan. 7, 1994

[51] Int. Cl.$^6$ .................. A61K 31/655; A61K 31/615
[52] U.S. Cl. ........................................... 514/150; 514/166
[58] Field of Search ..................................... 514/150, 166

[56] References Cited

U.S. PATENT DOCUMENTS 4,412,992  11/1983  Chan ........................................ 514/150

OTHER PUBLICATIONS

Stedman's Medical Dictionary, 24th Ed, Williams & Wilkins, Balto, MO, (1983), p. 297.
Bickel et al., "Gastric gel mucus thickness: Effect of distention, 16,16-dimethyl prostaglandin $E_2$ and carbenoxolone" *Gastroenterology* (1981) 80:770–775.
Miller, "Protective effects of prostaglandins against gastric mucosal damage: Current knowledge and proposed mechanisms" *Am. J. Physiol.* (1983) 245(Gastrointest. Liver Physiol. 8):G601–G623.
Bukhave et al., "Saturation kinetics applied to in vitro effects of low prostaglandin $E_2$ and $F_{2a}$ concentrations on ion transport across human jejunal mucosa" *Gastroenterology* (1980) 78:32–42.
Konturek et al., "Epidermal growth factor (EGF) and gastric cytoprotection. Role of endogenous prostaglandins (PGs) and DNA synthesis" *Gastroenterology* (1981) 80:1196.
Konturek et al., "Comparison of atropine and pirenzepine on gastric acid and serum hormonal responses to sham-feeding and gastric distention in duodenal ulcer (DU) patients" *Gastroenterology* (1981) 80:1196.
Konturek et al., "Generation of prostaglandins (PGs) in gastrointestinal mucosa of healthy subjects and duodenal ulcer (DU) patients" *Gastroenterology* (1981) 80:1196.
Konturek et al., "Ranitidine (R), a new potent $H_2$-receptor antagonist. Comparison with cimetidine (C) on gastric and pancreatic secretion in duodenal ulcer (DU) patients" *Gastroenterology* (1981) 80:1196.
Whittle et al., "Prostanoids as regulators of gastrointestinal function" *Physiology of the Gastrointestinal Tract*, Johnson, L. R., ed., (1987) 2nd Edition, Raven Press, New York, Chapter 6, pp. 143–180.
Kitahora et al., "Active oxygen species generated by monocytes and polymorphonuclear cells in Crohn's disease" *Dig. Dis. Sci.* (1988) 33:951–955.
Tauber et al., "Neutrophil oxygen reduction: The enzymes and the products" *Adv. Free Radical Biol. Med.* (1985) 1:265–307.
Ohlsson et al., "Localization of chymotrypsin-like cationic protein, collagenase and elastase in azurophil granules of human neutrophilic polymorphonuclear leukocytes" *Hoppe–Seylers Z. Physiol. Chem.* (1977) 358:361–366.
Lennard-Jones et al., "Cancer in colitis: Assessment of the individual risk by clinical and histological criteria" *Gastroenterology* (1977) 73:1280–1289.
Farmer et al., "Carcinoma associated with mucosal ulcerative colitis, and with transmural colitis and enteritis (Crohn's Disease)" *Cancer* (1971) 28:289–292.
Sipponen et al., "Atrophic chronic gastritis and intestinal metaplasia in gastric carcinoma" *Cancer* (1983) 52:1062–1067.
Reddy et al., "Metabolic epidemiology of large bowel cancer" *Mutation Res.* (1980) 72:511–522.
Armstrong et al., "Environmental factors and cancer incidence and mortality in different countries, with special reference to dietary practices" *Int. J. Cancer* (1975) 15:617–631.
Grisham, "Effect of 5-aminosalicylic acid on ferrous sulfate-mediated damage to deoxyribose" *Biochem. Pharmacol.* (1990) 39:2060–2063.
Mukai et al., "Mutagenicity of malonaldehyde, a decomposition product of perixodized polyunsaturated fatty acids" *Science* (1976) 191:868–869.
Basu et al., "Unequivocal demonstration that malondialdehyde is a mutagen" *Carcinogenesis* (1983) 4:331–333.
Basu et al., "Dissociation of malondialdehyde mutagenicity in *Salmonella typhimurium* from its ability to induce interstrand DNA cross-links" *Mutation Res.* (1984) 129:36–46.
Marnett, "Polycyclic aromatic hydrocarbon oxidation during prostaglandin biosynthesis" *Life Sci.* (1981) 29:531–546.
Adams et al., "The cell biology of macrophage activation" *Ann. Rev. Immunol.* (1984) 2:283–318.
Nathan et al., "Cellular component of inflammation: Monocytes and macrophages" *Textbook of Rheumatology* Kelley, W. N., et al., eds., W. B. Saunders Company, Philadelphia, (1981) Chapter 6, pp. 136–162.
Seilhamer et al., "Cloning and recombinant expression of phospholipase $A_2$ present in rheumatoid arthritic synovial fluid" *J. Biol. Chem.* (1989) 264:5335–5338.
Minami et al., "Raised serum activity of phospholipase $A_2$ immunochemically related to group II enzyme in inflammatory bowel disease: Its correlation with disease activity of Crohn's disease and ulcerative colitis" *Gut* (1992) 33:914–921.
Wright et al., "Purification of a cellular (granulocyte) and an extracellular (serum) phospholipase $A_2$ that participate in the (List continued on next page.)

Primary Examiner—Jerome D. Goldberg
Attorney, Agent, or Firm—Morrison & Foerster

[57] ABSTRACT

The present invention provides a method of colon cancer chemoprevention or chemotherapy comprising administering to an individual suffering from colon cancer or at risk to develop colon cancer a pharmaceutical composition comprising an effective amount of a 2-hydroxy-5-phenylazobenzoic acid derivative or an ester of an active metabolite thereof, or a pharmacologically acceptable salt of the 2-hydroxy-5-phenylazobenzoic acid derivative or an ester or an active metabolite thereof.

5 Claims, 4 Drawing Sheets

OTHER PUBLICATIONS destruction of *Escherichia coli* in a rabbit inflammatory exudate" *J. Biol. Chem.* (1990) 265:6675–6681.

Hayakawa et al., "The primary structure of rat platelet phospholipase $A_2$" *J. Biochem.* (1988) 104:767–772.

Lyons–Giordano et al., "Interleukin–1β stimulates phospholipase $A_2$ mRNA synthesis in rabbit articular chondrocytes" *Biochem. Biophys. Res. Commun.* (1989) 164:488–495.

Nakano et al., "Group II phospholipase $A_2$ mRNA synthesis is stimulated by two distinct mechanisms in rat vascular smooth muscle cells" *FEBS Lett.* (1990) 261:171–174.

Pfeilschifter et al. "Interleukin 1 and tumor necrosis factor synergistically stimulate prostaglandin synthesis and phospholipase A2 release from rat renal mesangial cells" *Biochem. Biophys. Res. Commun.* (1989) 159:385–394.

Oka et al., "Inflammatory factors stimulate expression of group II phospholipase $A_2$ in rat cultured astrocytes" *J. Biol. Chem.* (1991) 266:9956–9960.

Okada et al., "Generation of cytotoxic lipid substance in cell–mediated cytotoxicity" *Japan. J. Exp. Med.* (1975) 45:533–534.

Kristensen et al., "Two alternatively spliced mouse urokinase receptor mRNAs with different histological localization in the gastrointestinal tract" *J. Cell Biol.* (1991) 115:1763–1771.

Lund et al., "Urokinase receptor mRNA level and gene transcription are strongly and rapidly increased by phorbol myristate acetate in human monocyte–like U937 cells" *J. Biol. Chem.* (1991) 266:5177–5181.

Lund et al., "Urokinase–receptor biosynthesis, mRNA level and gene transcription are increased by transforming growth factor β1 in human A549 lung carcinoma cells" *EMBO J.* (1991) 10:3399–3407.

Stoppelli et al., "Differentiation–enhanced binding of the amino–terminal fragment of human urokinase plasminogen activator to a specific receptor on U937 monocytes" *Natl. Acad. Sci. USA* (1985) 82:4939–4943.

Pyke et al., "Urokinase–type plasminogen activator is expressed in stromal cells and its receptor in cancer cells at invasive foci in human colon adenocarcinomas" *Am. J. Pathol.* (1991) 138:1059–1067.

Ossowski et al., "In vivo paracrine interaction between urokinase and its receptor: Effect on tumor cell invasion" *J. Cell. Biol.* (1991) 115:1107–1112.

Narisawa et al., "Inhibition of development of methylnitrosourea–induced rat colon tumors by indomethacin treatment" *Cancer Res.* (1981) 41:1954–1957.

Pollard et al., "The suppressive effect of piroxicam on autochthonous intestinal tumors in the rat" *Cancer Lett.* (1983) 21:57–61.

Moorghen et al., "A protective effect of sulindac against chemically–induced primary colonic tumours in mice" *J. Pathol.* (1988) 156:341–347.

Reddy et al., "Aspirin inhibits cancer of the colon" *Gastroenterology* (1993) 104:A443.

Kune et al., "Colorectal cancer risk, chronic illnesses, operations, and medications: Case control results from the Melbourne colorectal cancer study" *Cancer Res.* (1988) 48:4399–4404.

Paganini–Hill et al., "Aspirin use and incidence of large–bowel cancer in a California retirement community" *J. Natl. Cancer Inst.* (1991) 83:1182–1183.

Labayle et al., "Sulindac causes regression of rectal polyps in familial adenomatous polyposis" *Gastroenterology* (1991) 101:635–639.

Klein et al., "The use of indomethacin, sulindac, and tamoxifen for the treatment of desmoid tumors associated with familial polyposis" *Cancer* (1987) 60:2863–2868.

Shen et al., "Chemical and biological studies on indomethacin, sulindac and their analogs" *Advances Drug Research* Harper, N. J., et al., eds., Academic Press, London (1977) 12:89–245. A title page and table of contents is included herewith.

Hucker et al., "Studies on the absorption, distribution and excretion of indomethacin in various species" *J. Pharmacol. Exp. Therap.* (1966) 153:237–249.

Reddy et al., "Inhibition of colon carcinogenesis by prostaglandin synthesis inhibitors and related compounds" *Carcinogenesis* (1992) 13:1019–1023.

Hubbard et al., "Profiles of prostaglandin biosynthesis in sixteen established cell lines derived from human lung, colon, prostate, and ovarian tumors" *Cancer Res.* (1988) 48:4770–4775.

Maxwell et al., "Enhanced secretion of prostaglandin $E_2$ by tissue–fixed macrophages in colonic carcinoma" *Digestion* (1990) 47:160–166.

Clive et al., "Renal syndromes associated with nonsteroidal antiinflammatory drugs" *New Engl. J. Med.* (1984) 310:563–572.

Langman, "Epidemiologic evidence on the association between peptic ulceration and antiinflammatory drug use" *Gastroenterology* (1989) 96:640–646.

Bjarnason et al., "Side effects of nonsteroidal anti–inflammatory drugs on the small and large intestine in humans" *Gastroenterology* (1993) 104:1832–1847.

Tanner et al., "Colonic inflammation and nonsteroidal anti–inflammatory drug administration" *Digestion* (1988) 41:116–120.

Langman et al., "Use of anti–inflammatory drugs by patients admitted with small or large bowel perforations and haemorrhage" *Br. Med. J.* (1985) 290:347–349.

Rampton et al., "Prostaglandin synthesis inhibitors in ulcerative colitis: Flurbiprofen compared with conventional treatment" *Prostaglandins* (1981) 21:417–425.

Grisham et al., "Effects of aminosalicylates and immunosuppressive agents on nitric oxide–dependent nitrosamine formation" *Gastroenterology* (1993) 104:A710.

Grisham et al., "Nitric oxide production by intestinal epithelial cells" *Gastroenterology* (1993) 104:A710.

Yamada et al., "Mucosal injury and inflammation in a model of chronic granulomatous colitis in rats" *Gastroenterology* (1993) 104:759–771.

USE OF 2-HYDROXY-5-PHENYLAZOBENZOIC ACID DERIVATIVES AS COLON CANCER CHEMOPREVENTATIVE AND CHEMOTHERAPEUTIC AGENTS

TECHNICAL FIELD

This invention is related to colon cancer chemoprevention and chemotherapy.

BACKGROUND ART

Colon cancer currently accounts for 11% of all deaths due to malignancy annually in the United States. With an incidence of 62 per 100,000 and a prevalence of 300 per 100,000, the disease is currently the third leading cause of death in men and the fourth leading cause of death in women. Colon cancer has a particularly poor five-year survival rate of less than 50%, due to the late stage at which diagnosis is generally made. The currently favored treatment, surgery combined with chemotherapy, has failed to increase this survival rate. What is needed is a safe and effective preventive therapy which could be initiated early in patient populations known to be at an increased risk of developing colon cancer.

Eicosanoids and Differentiated Functions of Gastrointestinal Cells. Eicosanoids are significant regulators of gastrointestinal epithelial cell growth, differentiation and function. Eicosanoid products of the prostaglandin series are known to induce mucus secretion (Beckel and Kauffman (1981) *Gastroenterology* 80:770–776) and the secretion of electrolytes and fluid (Miller (1983) *Am. J. Physiol.* 245:G601-G623). They also induce active transport (Bukhave and Rask-Madsen (1980) *Gastroenterology* 78:32–37) and increase the replicative capacity of the epithelium (Konturek et al. (1981) *Gastroenterology* 80:1196–1201). These responses result in the maintenance of a differentiated, protective barrier system of tightly joined epithelial cells whose apical surface are covered by a dense glyco-conjugate chemical buffer. In the stomach and upper duodenum such a barrier protects against the acidic and proteolytic environment elaborated for digestion, while in the colon it protects against the invasion of bacteria and toxins. It is therefore not surprising that exogenous, synthetic prostaglandins are actively cytoprotective (Whittle and Vane (1987) In: Johnson (ed.) PHYSIOLOGY OF THE GASTROINTESTINAL TRACT, VOl. 1, 2nd ed., New York: Raven Press, pp. 143–180) and have found therapeutic utility as secondary anti-ulcer treatments. The gastrointestinal ("GI") system has therefore evolved to actively produce and rely on a specific differentiated complement of eicosanoid products present in the local environment. As all eicosanoids are derived from the common precursor arachidonic acid, which is itself liberated from membrane phospholipids, GI mucosal cells have a relatively high basal level of arachidonate turnover initiated by the enzyme phospholipase $A_2$ ($PLA_2$).

The GI system is also a primary defense mechanism against environmental bacteria, antigens and toxins and must therefore also possess the ability to mount an aggressive and rapid inflammatory response. This response also relies upon eicosanoid products of both the prostaglandin (PG) series as well as the chemotactic leukotriene series (LTs) and results in the influx of blood-borne neutrophils, macrophages and immune cells in response to the activating agent. Each of these invading cells also brings with it a capacity to metabolize its own phospholipids as well as mucosal and luminal phospholipids by releasing inflammatory (secreted) $PLA_2$ to amplify the release of arachidonic acid, which is then metabolized into both PGs and LTs.

Although the inflammatory cell infiltration confines and destroys the offending stimulus, the extent of damage due to inflammatory cell release products is significant. Neutrophils and macrophages release superoxide ($O_2^-$) (Kitahora et al. (1988) *Dig. Dis. Sci.* 33:951–955) as well as hydrogen peroxide ($H_2O_2$) (Tauber and Babior (1985) *Free Radic. Biol. Med.* 1:265–307), and proteases (Ohlsson et al. (1977) *Hoppe Seylers Z. Physiol. Chem* 358:361–366). Where the resultant infiltration is extensive, significant denudation of the epithelial layer occurs with a subsequent compromise of the barrier function. Resolution of the inflammatory response is then required to regain final optimal epithelial barrier coverage.

Chronic GI Inflammation and GI Cancer Induction. It is now well documented that chronic gastrointestinal inflammatory diseases such as ulcerative colitis (Lennard-Jones et al. (1977) *Gastroenterology* 73:1280–1285), Crohn's disease (Farmer et al. (1971) *Cancer* 28:289–295), and chronic atrophic gastritis (Sipponen et al. (1983) *Cancer* 52:1062–1067) are associated with an increased risk of subsequent gastrointestinal cancer. Although the mechanisms are not yet proven, three important intersecting pathways which could lead to subsequent transformation, heightened proliferation and malignant invasion occur during multiple acute inflammatory episodes. As discussed below these are: (1) increased colonic free radical and carcinogen load, (2) altered regulation of trophic eicosanoids, and (3) induction of gene products which mediate cellular invasion.

Altered carcinogen load due to inflammatory episodes. The colon may be uniquely exposed to a fairly high basal load of genotoxic carcinogens and tumor promoters resulting from the metabolism of dietary compounds and endogenous secretions such as bile acids by colonic bacteria. A relationship between fecal carcinogens and colon cancer induction is supported by findings of increased mutagens in the stools of high-risk individuals versus those of low-risk populations (Reddy et al. (1980) *Mut. Res.* 72:511–515). This correlation is also consistent with repeated findings showing a negative association between dietary fiber intake and incidence of colon cancer (Armstrong and Doll (1975) *Int. J. Cancer* 15:617–623). The protective effect of fiber is postulated to occur through an increase in stool volume which results in a dilution of stool carcinogens and decreased transmit time, leading to more rapid carcinogen elimination. These results raise the possibility that if a reduction in concentration of the stool carcinogen load can lead to a decreased cancer risk, then an increase in the carcinogen load may lead to an increased risk. One such increase in colonic carcinogens could be derived from successive inflammatory events.

A particularly relevant example is the inflammatory neutrophil production of carcinogenic nitrosamines via the L-arginine-dependent formation of nitrogen oxides as nitric oxide (Grisham (1993) *Gastroenterology* 104:A243). Other oxidative products released by inflammatory cells include superoxide as well as hydrogen peroxide, which in the presence of certain transition metals such as iron (Fe) can generate the highly reactive and cytotoxic hydroxyl radical (OH:) (Grisham (1990) *Biochem Pharmacol* 39:2060–2063). In addition to the increased carcinogen and free radical load elaborated by the influx of inflammatory cells, the arachidonic acid cascade is also known to be capable of producing mutagenic metabolites. A metabolite of prostaglandin H2 (PGH2), malondialdehyde (MDA), is a direct acting mutagen in vitro (Mukai and Goldstein (1976) *Science* 191:868–869) and a carcinogen in animals (Basu and Marnett (1983) *Carcinogenesis* 4:331–333) and can be enzymatically produced by thromboxane synthetase in high yields in cells with an active cyclooxygenase pathway. MDA has been shown to produce frameshift mutations similar to those associated with the human colon p53 gene (Marnett, et al. (1985) *Mutat. Res.* 129:36–46). PGH synthase itself is a potent peroxidase and has been shown to catalyze the activation of a wide range of polycyclic hydrocarbons to mutagens (Marnett (1981) *Life Sci.* 29:531–546).

These findings suggest that chronic and aberrant (inflammatory cell driven) activation of the arachidonic acid cascade in the gastrointestinal tract is one pathway which can lead to an increased carcinogen load with the potential induction of DNA mutations during times of maximum DNA synthesis. Increased cell proliferation, which follows epithelial denudation induced by invading inflammatory cells, could lead to an increased number of cells susceptible to the action of such carcinogens. Alternatively, increased proliferation could serve to amplify mutations (through clonal expansion) induced previously by carcinogens.

Altered eicosanoid regulation can drive proliferation due to inflammatory episodes. An additional mechanism linking GI inflammation and the progression of GI cancers could be a disruption in normal eicosanoid regulation. As discussed above, the normal differentiated functions of the GI mucosal epithelium are intimately linked to the diverse range of biological activities affected by endogenous eicosanoids. Since these agents act locally and generally have short half-lives due to active metabolic inactivation, periods of acute inflammatory events will dramatically alter the normal regulation of eicosanoid homeostasis.

Upon neutrophil and macrophage invasion into an inflammatory site these normal dynamics are dramatically altered. First, inflammatory cells bring with them a wide range of additional agonists such as cytokines, proteases and growth factors (Adams and Hamilton (1984) *Ann. Rev. Immunol.* 2:283–318, Ohlsson et al. (1977) *Physiol. Chem.* 358:361–366, Nathan and Cohn (1980) In: Kelly et al. (eds.), *Textbook of Rheumatology*, New York: W. B. Saunders, pp. 186–215), which by themselves chronically activate cellular $PLA_2$ ($cPLA_2$) to release arachidonic acid. Second, inflammatory cells are a rich source of additional forms of $PLA_2$ known as secretory or $sPLA_2$ (Seilhamer et al. (1989) *J. Biol. Chem.* 264:5335–5338). whose activities in GI inflammatory disease has recently been documented (Minami et al. (1992) *Gut* 33:914–921).

Unlike $cPLA_2$, $sPLA_2$ is released from inflammatory cells (Wright et al. (1990) *J. Biol. Chem.* 265:6675–6681), platelets (Hayakawa et al. (1988) *J. Biochem.* 104:767–772), chondrocytes (Lyons-Goirdano et al. (1989) *Biochem. Biopys. Res. Commun.* 64:488–495) and smooth muscle cells (Nakano et al. (1990) *FEBS Lett.* 261:171–174) by cytokines (Pfeilscifter et al. (1989) *Biophys. Res. Commun.* 159:385– 394), and, in particular, by endotoxin (Oka and Arita (1991) *J. Biol. Chem.* 266:9956–9960). In addition, because the extracellular milieu contains maximal calcium concentrations, $sPLA_2$ is unregulated once released. Upon release it therefore actively hydrolyses arachidonic acid and other fatty acids from the sn-2 position of phospholipids found in cellular and bacterial membranes as well as those from dietary and lipoprotein sources. The lysophospholipid resulting from removal of the sn-2 fatty acid from many such phospholipids is potently lysogenic for surrounding cells (Okada and Cyong (1975) *Jpn. J. Exp. Med.* 45:533–534).

Thus, this reaction can also lead to epithelial cell lysis and denudation in the unfiltered area, ultimately requiring enhanced proliferation to maintain the barrier function.

Inflammatory response and activation of genes directing cellular invasion. The inflammatory response not only disrupts normal eicosanoid regulation but also leads to the activation of gene products required for cellular invasion. One such product, the urokinase plasminogen activator receptor (uPAR), is normally expressed by intestinal epithelial cells. Its anchorage to the cell surface may be an important determinant of normal crypt cell migration and desquamation via cell surface proteolysis (Kristensen et al. (1991) *J. Cell. Biol.* 115:1763–1771). In inflammatory cells, uPAR gene expression is induced by activators of protein kinase C, by tumor promoters such as the phorbol ester TPA (Lund et al. (1991) *J. Biol. Chem.* 266:5177–5181), and by various cytokines (Lund et al. (1991) *EMBO J.* 10:3399–3401) which induce an invasive phenotype required for tissue infiltration (Stoppelli et al. (1985) *Natl. Acad. Sci. USA* 82:4939–4943). It is therefore not surprising that high levels of uPAR expression have also been detected in several tumor cell lines with metastatic potential, including colon cancer-derived cells (Pyke et al. (1991) *Am. J. Pathol.* 138:1059–1067). Of particular interest are co-culture experiments showing that invasive potential was more highly correlated with expression of uPAR than its ligand plasminogen activator (Ossowski et al. (1991) *J. Cell. Biol.* 15:1107–1112). Thus, multiple cycles of inflammatory responses could also contribute to uPAR overexpression in colonic mucosal cells, resulting in the acquisition of an invasive phenotype in a previously benign tumor.

GI mucosal cells may therefore be uniquely sensitive to chronic inflammatory episodes because of three intersecting pathways: (1) the epithelial cells are positioned in an environment with a high carcinogen load which can further increase during inflammatory episodes; (2) the products of both the endogenous and infiltrated eicosanoid cascades are trophic agents; and (3) their own differentiated response to inflammatory agents includes expression of gene products required for acquisition of an invasive phenotype. Together these three paths could lead to a transformation event and resultant tumor induction, progression and invasion. Therefore, agents which block certain arms of the eicosanoid cascade are useful in colon cancer chemoprevention.

NSAIDs and Colon Cancer Chemoprevention. There is evidence that several non-steroid antiinflammatory drugs (NSAIDs) are effective in reducing the number of tumor-bearing animals and tumor incidence per animal in rat models of colon carcinogenesis. (Narisawa et al. (1981) *Cancer Res.* 41:1954–1957), (Pollard et al. (1983) *Cancer Lett.* 21:57–61) (Moorghen et al. (1988) *J. Pathol.* 156:341–347) (Reddy et al. (1993) *Gastroenterology* 104:A443) where up to a 70% reduction in tumor incidence has been noted at doses of 80% of the maximum tolerated dose. In a study of dimethylhydrazine-induced colon carcinogenesis, sulindac was observed to reduce tumor incidence only when present during carcinogen administration, but not if given 17 weeks following the carcinogen (Moorghen et al. (1988) *J. Pathol.* 156:341–347).

In several retrospective studies, aspirin intake has been assessed as a chemopreventive therapy in ensuing colon cancer incidence. The results of these studies have ranged from a halving (Kune et al. (1988) *Cancer Res.* 48:4399–4404) of the risk of colon cancer development to a 50% increased risk (Paganini-Hill et al. (1991) *J. Natl. Cancer Inst.* 83:1182–1183). It should be noted, however, that any human study employing aspirin and other NSAIDs, especially retrospective studies, could be flawed by the induced frequency of GI bleeding which may allow for earlier detection of the polyp or tumor in the NSAID group through occult blood screening and sigmoidoscopy.

Although the retrospective aspirin studies have provided equivocal results, the initial results for certain NSAIDs found in animal studies, summarized above, have been replicated in prospective human trials. The NSAID, sulindac, has been shown in a randomized, placebo-controlled, double-blind crossover study to cause regression of polyps in nine familial polyposis patients in less than 4 months (Labayle et al. (1991) *Gastroenterology* 101:635–639). In addition, polyp growth resumed following sulindac withdrawal. This finding is significant because a similar study using indomethacin found no influence on polyp regression (Klein et al. (1987) *Cancer* 60:2863–1868). Although both of these NSAIDs derive their anti-inflammatory activity from inhibition of cyclooxygenase, sulindac is a prodrug which is converted to its active metabolite, sulindac sulfide, by the colonic bacteria (Shen and Winter (1975) *Adv. Drug. Res.* 12:89–245). In contrast, indomethacin is ingested in its active form, where it is absorbed primarily from the upper GI tract for systemic delivery (Hucker et al. (1966) *J. Pharmacol. Exp. Ther.* 153:237–249). It is therefore likely that the concentrations of active metabolite delivered by sulindac to the colon are significantly higher than from indomethacin. This result suggests that a significant portion of the observed NSAID chemopreventive effect is derived from local action of the drug at the mucosal-lumen interface.

Although this evidence of NSAID-induced inhibition of colonic tumor incidence in animal models suggests a mechanism of inhibition via the tumor cell cyclooxygenase, confirmation of such a mechanism is lacking. Tumor tissue excised from NSAID-treated animals has been shown to secrete dramatically reduced levels of $PGE_2$, which is consistent with this hypothesis (Reddy et al. (1992) *Carcinogenesis* 13:1019–1023). However, most colonic tumors are heterogeneous with respect to their resident cell types, and several reports have documented that epithelial cell lines generated from colorectal adenocarcinomas are not high producers of $PGE_2$ or other prostanoids (Hubbard et al. (1988) *Cancer Res.* 48:4770–4775). A report on the eicosanoid production of cells fractionated from human colon tissue, however, showed that tumor epithelial cells produced $PGE_2$ levels similar to uninvolved tissue, while tumor-derived mononuclear cells showed significantly greater eicosanoid synthesis than their normal counterparts (Maxwell et al. (1990) *Digestion* 47:160–166). Therefore, target cells sensitive to NSAID inhibition may not be the tumor epithelial cells, but could be some other resident producing high PG levels to which the epithelial cells are responsive.

Profile of the Preferred Chemopreventive Therapy All NSAIDs carry significant side effect profiles. NSAIDs are not tissue specific in their inhibition of cyclooxygenase products, and both renal and gastrointestinal systems are particularly sensitive. NSAIDs reduce renal perfusion resulting in nephrotoxicity (Clive and Stoff (1984) *N. Engl. J. Med.* 310:563–572), and because prostaglandins are necessary for the normal differentiated functions of the GI epithelium, NSAID induced gastric ulceration is a significant contributor to morbidity and mortality associated with this class of drugs (Langman (1989) *Gastroenterology* 96:640–646, Bjarnason et al. (1992) *Gastroenterology* 104:1832– 1847). In the lower bowel, chronic NSAID therapy has been reported to result in colitis ranging from proctitis to pancolitis (Tanner and Raghunat (1988) *Digestion* 41:116–120). In one retrospective study, it was estimated that NSAID ingestion was found in 25% of patients presenting with large and small bowel perforation and bleeding (Langman et al. (1985) *Br. Med. J.* 290:347– 349). Finally, in patients with existing chronic inflammatory bowel diseases, who are already at high risk of developing colorectal cancer, non-5-ASA-containing NSAIDs as well as aspirin therapy is contraindicated due to exacerbation of the existing disease condition (Rampton and Sladen (1981) *Prostaglandins* 21:417–425). The ideal drug for colon cancer chemoprevention is, therefore, one with the following profile:

1) Colon specific—It should be a prodrug with no activity elaborated in the upper GI tract, but converted to active form upon reaching the colon (sulindac-like);

2) Limited absorption—Absorption of the parent and metabolites should be minimal, especially once converted to its active form;

3) Lack of systemic activity—Once absorbed, metabolic inactivation should convert the drug to an inactive form, thereby limiting systemic effects on the renal and GI systems;

4) Antioxidant properties—Colon-specific antioxidant activity would further serve to lower the carcinogen burden; and

5) NSAID-like anti-inflammatory mechanism—The active metabolite should inhibit inflammation-induced eicosanoid pathways, however, eicosanoid inhibition without compromise to basal maintenance pathways would be preferred.

To summarize, certain NSAIDs have been shown to inhibit colon tumor incidence in carcinogen-induced animal models and inhibit polyp growth in humans. Although the mechanism for tumor inhibition by NSAIDs is unproven, these drugs may modulate gastrointestinal eicosanoid production and metabolism. Unfortunately, NSAIDs also have a disturbing and serious gastrointestinal side effect profile which may preclude their chronic use. Therefore, it would be highly desirable to identify NSAIDs which are effective as chemopreventive agents but which lack these side effects.

Chan, U.S. Pat. No. 4,412,992, describes the preparation of 2-hydroxy-5-phenylazobenzoic acid derivatives and their use in the treatment of ulcerative colitis.

DISCLOSURE OF THE INVENTION

In accordance with one embodiment of the present invention, there is provided a method of treating an individual suffering from colon cancer or at risk to develop colon cancer comprising administering to the human an effective amount of a pharmaceutical composition comprising a 2-hydroxy-5-phenylazobenzoic acid derivative of the general formula:

wherein X is an —SO— or —CO— group and R is either a phenyl or carboxymethylphenyl radical or is a radical of the formula —$(CH_2)_n$—Y, in which Y is a hydroxyl group, an amino group, a monoalkyl- or dialkyl-amino group, the alkyl moieties of which contain up to 6 carbon atoms, or a carboxylic or sulphonic acid group, and n is a whole number of from 1 to 6, and in which one or more of the hydrogen atoms in the alkylene radical can be replaced by amino groups, monoalkyl- or dialkyl-amino groups, the alkyl moieties of which contain up to 6 carbon atoms, or alkyl radicals, and in which the —(CH$_2$)$_n$—Y radical is either attached directly to the nitrogen atom or via a benzene ring, with the proviso that R—NH—X— is other than a —CO—NHCH—CH$_2$—COOH radical; or an ester or active metabolite thereof, or a non-toxic, pharmacologically acceptable salt of the 2-hydroxy-5-phenylazobenzoic acid derivative or ester or active metabolite thereof.

In accordance with another embodiment of the present invention, the pharmaceutical composition of the method consists essentially of the 2-hydroxy-5-phenylazobenzoic acid derivative or ester or active metabolite thereof or a salt of the 2-hydroxy-5-phenylazobenzoic acid derivative or an ester or an active metabolite thereof in admixture with a solid or liquid pharmaceutical diluent or carrier.

In yet another embodiment of the present invention, the 2-hydroxy-5-phenylazobenzoic acid derivative is balsalazide.

In a further embodiment of the present invention, the active metabolite is 5-ASA.

In still a further embodiment of the present invention, the pharmaceutical composition is administered orally to an individual suffering from or at risk to develop colon cancer in a daily dosage ranging from 1 to 14 g per 70 kg body weight per day of the 2-hydroxy-5-phenylazobenzoic acid derivative or an ester or an active metabolite thereof or a salt of the 2-hydroxy-5-phenylazobenzoic acid derivative or an ester or an active metabolite thereof.

In another embodiment of the present invention, the pharmaceutical composition is administered rectally to an individual suffering from or at risk to develop colon cancer in a daily dosage ranging from 1 to 14 g per 70 kg body weight per day of the 2-hydroxy-5-phenylazobenzoic acid derivative or an ester or an active metabolite thereof or a salt of the 2-hydroxy-5-phenylazobenzoic acid derivative or an ester or an active metabolite thereof.

MODES FOR CARRYING OUT THE INVENTION 2-hydroxy-5-phenylazobenzoic acid derivatives, particularly balsalazide and its active metabolites, have been found to be effective in colon cancer chemoprevention. These 2-hydroxy-5-phenylazobenzoic acid derivatives have the following general formula:

wherein X is an —SO$_2$— or —CO— group; and R is either a phenyl or carboxymethylphenyl radical or is a radical of the formula —(CH$_2$)$_n$—Y, in which Y is a hydroxyl group, an amino group, a monoalkyl- or dialkyl-amino group, the alkyl moieties of which contain up to 6 carbon atoms or a carboxylic or sulphonic acid group, and n is a whole number of from 1 to 6, and in which one or more of the hydrogen atoms in the alkylene radical can be replaced by amino groups, monoalkyl- or dialkyl-amino groups, the alkyl moieties of which contain up to 6 carbon atoms or alkyl radicals, and in which the —(CH$_2$)$_n$—Y radical is either attached directly to the nitrogen atom or via a benzene ring, with the proviso that R—NH—X— is other than a —CO—NH—CH— CH$_2$—COOH radical.

As employed herein, the term "2-hydroxy-5-phenylazobenzoic acid derivative" also embraces esters or active metabolites of the compound or non-toxic, pharmacologically acceptable salts of the compound or its esters or active metabolites.

The term "active metabolite" refers to the products of the metabolism of 2-hydroxy-5-phenylazobenzoic acid derivatives in the human body, e.g., via the action of colonic bacteria, which inhibit colon cancer cell proliferation. For example, as discussed below, 5-ASA is an active metabolite of balsalazide.

Balsalazide sodium is a colonic-specific, non-steroidal, anti-inflammatory aminosalicylate which is useful in the treatment of active ulcerative colitis. Balsalazide as well as one of it's primary metabolites inhibits the growth of cultured human colon cancer cells and balsalazide inhibits aberrant crypt formation in animals treated with the carcinogen, azoxymethane. Like other NSAIDs, balsalazide is effective in human colorectal cancer chemoprevention. However, balsalazide has three important safety advantages: (1) the delivery of the drug is colon-specific; (2) no evidence of gastric or duodenal ulceration has been observed; and (3) no evidence of nephrotoxicity has been reported among over 500 patients treated to date, some for as long as three years. Balsalazide therefore possesses an ideal combination of efficacy and safety for the chemoprevention of colon cancer.

Figure 1:
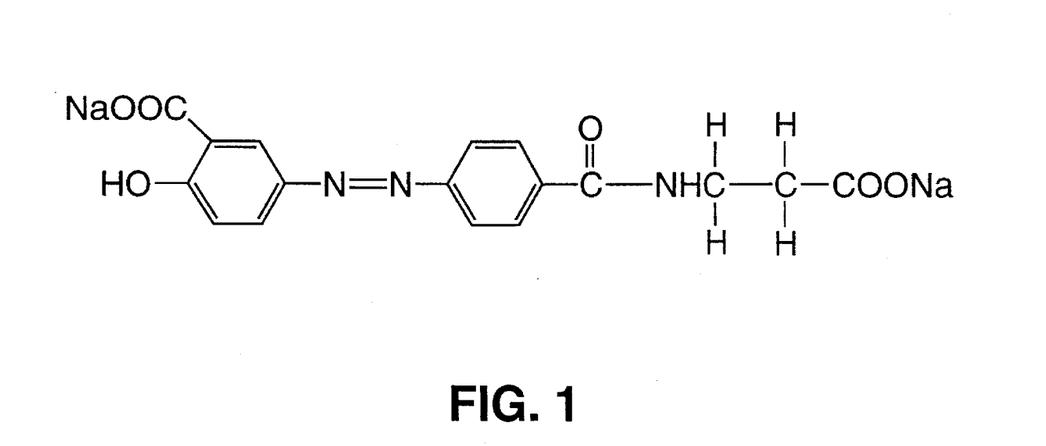
FIG. 1 shows the chemical structure of a 2-hydroxy-5-phenylazobenzoic acid derivative wherein the generic name is balsalazide. The aminosalicylate moiety, 5-aminosalicylic acid (5-ASA) is linked to a carrier molecule, 4-aminobenzoyl-β-alanine (4-ABA), through an azo-bond.

Colon-specific delivery. Balsalazide is a prodrug the inactive form of which, like sulindac, is converted to an active antiinflammatory drug by the action of colonic bacteria. As shown in FIG. 1, balsalazide links the aminosalicylate 5-aminosalicylic acid (5-ASA) to an inert carrier molecule, 4-aminobenzoyl-β-alanine (4-ABA), through an azo-bond. Bacterial azoreductase hydrolyses this bond, releasing the 5-ASA for local action.

Limited systemic absorption. Balsalazide, when taken orally, passes uncleaved and virtually unabsorbed through the upper GI tract. As little as 0.3% of the ingested dose of the prodrug is found in plasma or urine, with 99% of the drug reaching the colon intact. In the colon, the drug undergoes hydrolysis to form 5-ASA and 4-ABA, which interact with the colonic mucosa and are converted to their N-acetyl forms. The majority of 5-ASA resulting from a single dose of balsalazide is converted over a 96-hour period to N-acetyl-5-ASA (Nac5ASA) and excreted in the urine, while the 4-ABA and its N-acetyl metabolite are poorly absorbed. Since the N-acetyl metabolite of 5-ASA is inactive, systemic activity of delivered 5-ASA is also reduced (Chan et al. (1983) *Dig. Dis. Sci.* 28: 609–615).

Antioxidant properties. As discussed previously, a chemopreventive agent which possesses effective antioxidant properties can also contribute to a reduction in the colonic carcinogen load as well as reducing the damage induced by free radical release from invading inflammatory cells. 5-ASA inhibits nitrosamine formation from argininedependent nitric oxide (Grisham (1993) *Gastroenterology* 104:A243). In addition, both intact balsalazide and 5-ASA are effective free radical scavengers against $O_2$- and OH:. Balsalazide and 5-ASA, when incubated with rectal biopsies from patients with ulcerative colitis, reduce rectal mucosal reactive oxygen metabolite production by over 90%. Both agents are also more effective than the anti-oxidants taurine, ascorbate or N-acetyl cysteine when used at similar concentrations (Simmonds et al. (1992) *Gastroenterology* 102: A696).

Colonic antiinflammatory activity without upper GI effects. Balsalazide possesses anti-inflammatory activity in several animal models of colonic inflammation, as well as in patients with active (Green et al. (1993) *Gastroenterology* 104:A709) and quiescent (Gaiffer et al. (1992) *Ailment. Pharmacol. Ther.* 6:479–485) ulcerative colitis. Importantly, the drug displays excellent gastrointestinal tolerance.

Balsalazide and 5-ASA inhibit colon cancer cell proliferation in vitro. 5-ASA, as well as balsalazide, show significant growth inhibitory activity against human colon cancer cells.

Methods of Colon Cancer Chemoprevention and/or Chemotherapy.

2-hydroxy-5-phenylazobenzoic acid derivatives of the present invention, particularly balsalazide and its metabolites, are, therefore, useful for colon cancer chemotherapy. They will preferably be administered to human individuals suffering from colon cancer or at risk to develop colon cancer in the form of pharmaceutical compositions comprising the 2-hydroxy-5-phenylazobenzoic acid derivative(s). The pharmaceutical composition may also comprise one or more non-toxic pharmaceutically acceptable carriers, excipients, and/or diluents. Oral administration is preferred. Standard pharmaceutical formulation techniques are used, such as those disclosed in *Remington's Pharmaceutical Sciences*, Mack Publishing Co., Easton, Pa., latest edition.

The compositions may be in the form of tablets, capsules, powders, granules, lozenges, liquid or gel preparations. Tablets and capsules for oral administration may be in a form suitable for unit dose presentation and may contain conventional excipients. Examples of these are: binding agents such as syrup, acacia, gelatin, sorbitol, tragacanth, and polyvinylpyrrolidone; fillers such as lactose, sugar, maize-starch, calcium phosphate, sorbitol or glycine; tableting lubricants, such as magnesium stearate, silicon dioxide, talc, polyethylene glycol or silica; disintegrants, such as potato starch; or acceptable wetting agents, such as sodium lauryl sulfate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, e.g., sorbitol, syrup, methyl cellulose, glucose syrup, gelatin, hydrogenated edible fats, emulsifying agents, e.g., lecithin, sorbitan monooleate, or acacia; non-aqueous vehicles (including edible oils), e.g., almond oil, fractionated coconut oil, oily esters such as glycerine, propylene glycol, or ethyl alcohol; preservatives such as methyl or propyl p-hydroxybenzoate or sorbic acid, and, if desired, conventional flavoring or coloring agents.

The percentage of active material in the pharmaceutical compositions of the present invention may be varied, it being necessary that it should constitute a proportion such that a suitable dose for the desired therapeutic effect shall be obtained. In general, the preparations of the present invention should be administered orally or rectally to humans to give 1 to 14 g of active substance per day per 70 kg of body weight.

The following examples are offered by way of illustration and not by way of limitation.

EXAMPLES

EXAMPLE 1

Balsalazide and 5-ASA inhibit colon cancer cell proliferation in vitro

The activity of balsalazide and its metabolite 5ASA on the growth of human colon cancer cells was demonstrated in vitro using the human adenoma cells HT-29 and LS174T. Cells were grown in Dulbeccos Modified Eagle medium supplemented with 10% calf serum in an atmosphere of 5% $CO_2$ at 37° C. For growth experiments, cells were seeded into 24-well tissue culture dishes ($2cm^2$/well) at a density of 20,000 cells/well and allowed to attach for 12 hours. The growth medium was then changed and replaced with fresh media containing the test drugs.

Figure 2:
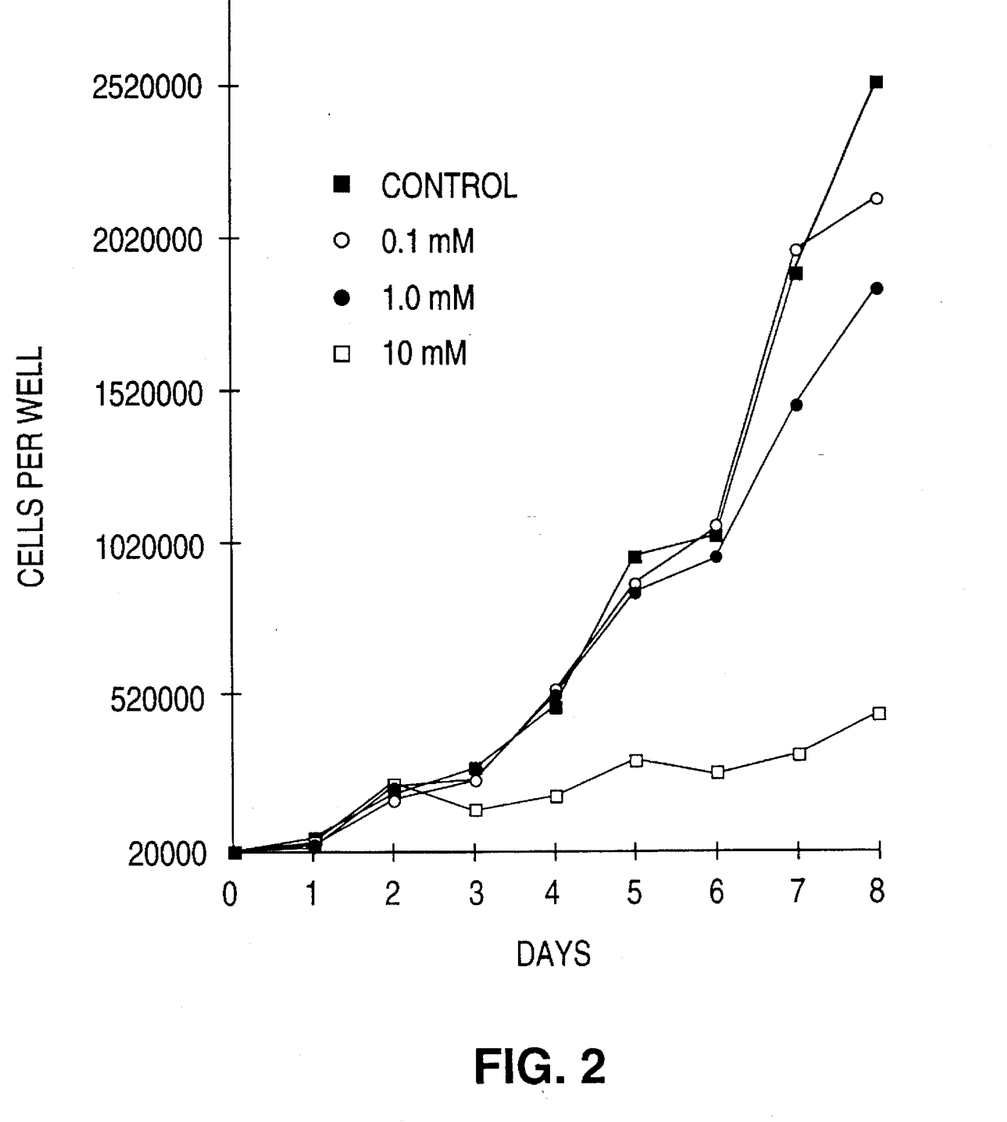
FIG. 2 shows the effects of 5-ASA on proliferation of the adenocarcinoma cell line HT-29 at doses of 0, 0.1, 1.0 and 10 mM. The cell numbers shown are the average of triplicate experiments.
Figure 3:
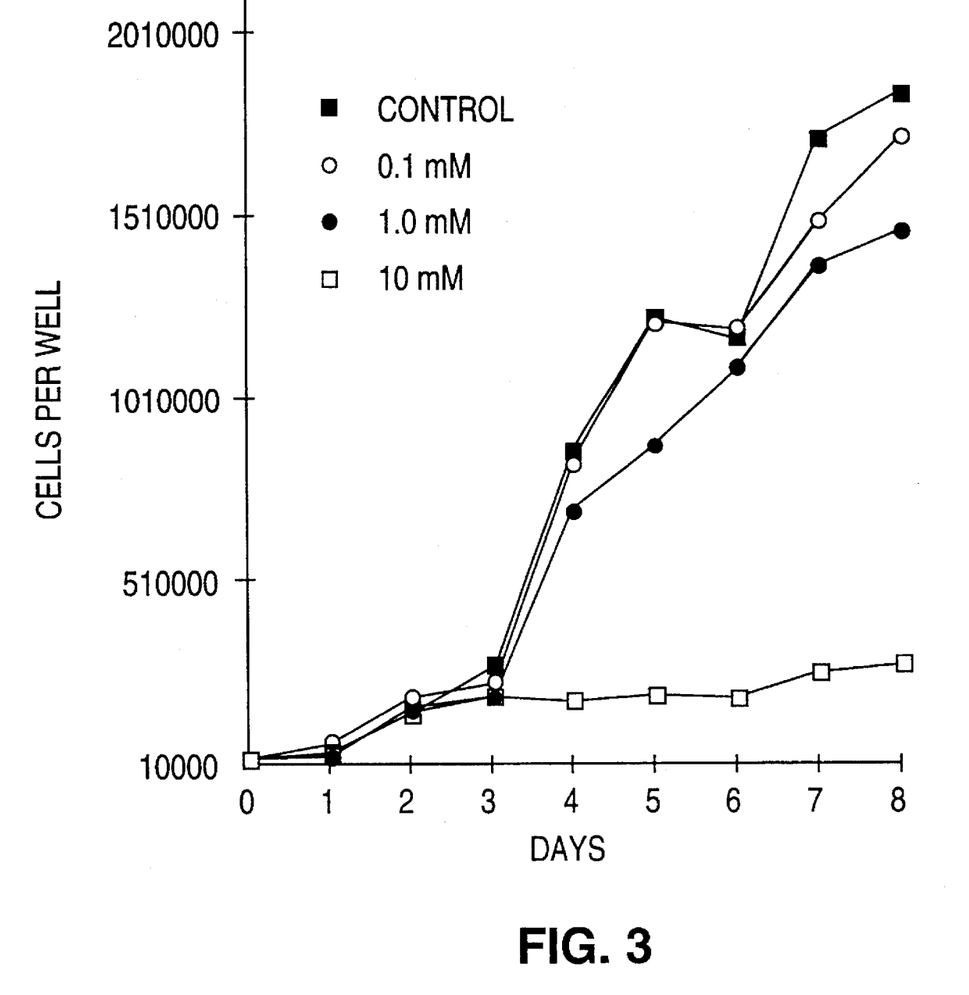
FIG. 3 shows the effects of 5-ASA on proliferation of the adenocarcinoma cell line LS174T at doses of 0, 0.1, 1.0 and 10 mM. The cell numbers shown are the average of triplicate experiments.

The test drugs were dissolved in tissue culture media at the desired concentration and added to individual wells. To determine the number of cells per well, media was removed and the cells washed with phosphate buffered saline solution. The cells were then incubated 15 minutes with trypsin-EDTA solution until detached. The detached cells were then removed from the wells and counted using a Coulter Counter (Model ZBI). As shown in FIGS. 2 and 3, both human colon cancer cell lines HT-29 and LS174T were growth inhibited by progressively greater concentrations of 5-ASA. At a dose of 10 mM 5-ASA inhibition reached 82% and 85%, respectively.

Comparative studies were also carried out to test the effectiveness of balsalazide with its two metabolites, 5-ASA and 4-ABA as well as with acetyl salicylic acid (aspirin) on cancer cell proliferation. As shown in Table 1, acetylsalicylic acid, which covalently inhibits cycloxygenase, was potently inhibitory in this assay, as was the parent drug balsalazide. However, 4-ABA, the carrier molecule of balsalazide, was inactive. The cell numbers shown in Table 1 are the average of triplicate culture wells.

TABLE 1

| Condition | Dose | HT-29 | | LS174T | |
|---|---|---|---|---|---|
| | | Cell No. on Day 10 | % of Control Cells | Cell No. on Day 10 | % of Control Cells |
| Control | — | 1315800 | — | 709750 | — |
| Ac-salicylic acid | (10 mM) | 14625 | 1.11 | 8300 | 2.24 |
| Balsalazide | (10 mM) | 47500 | 3.60 | 24925 | 3.51 |
| 5-ASA | (10 mM) | 512825 | 38.97 | 8675 | 1.22 |
| 4-ABA | (10 mM) | 1316625 | 100.06 | 768700 | 108.30 |

EXAMPLE 2

Influence of balsalazide and metabolites on aberrant crypt formation in the rat

Aberrant crypts were originally described in carcinogen-induced colonic mucosa as crypts of "increased size, thicker epithelial lining and increased pericryptal zones" (Bird et al. (1989) *Cancer Surv.* 8:189–200). NSAIDs are among the most potent inhibitors of aberrant crypt formation induced by the carcinogen, azoxymethane (AOM) in the rat (Wargovich et al. (1992) *J. Cell. Biochem.* 16G:51–54). The anti-tumor activity of several of these agents has been confirmed in longer term AOM animal studies. The aberrant crypt model is, therefore, an ideal in vivo assay for efficacy of balsalazide and metabolites.

Inhibition of Aberrant Crypt Induction. The efficacy of balsalazide (BSZ), and its metabolites, 5-aminosalicylic acid (5-ASA) and 4-aminobenzoyl-β-alanine (4-ABA) on the inhibition of aberrant crypt formation was determined in a model of colon cancer induced by azoxymethane (AOM) in the rat.

Four groups of 5 male F344 rats were used. Animals were 6–8 weeks of age at the start of dosing with a starting weight range within ±20% of the overall mean. The expected response to AOM treatment from published studies is the formation of 100–140 aberrant crypts per animal (Wargovich et al. (1992) *J. Cell. Biochem.* 16G:51–54). Using these response rates and a chi square analysis with 95% confidence limits, the sample size of 5 animals per group allows detection of statistically significant inhibition (at the $p<0.05$ level) by the test drugs when up to 50–75 aberrant crypts per animal are observed.

Animals were acclimatized for 10 days prior to being randomized into the test groups by body weight classes. Test drug was dissolved in the drinking water at a concentration which gave the desired dose per animal per day based on an average water consumption of 50 ml per day per animal Two groups were allowed one week of drug treatment prior to the AOM injections. Carcinogenesis was induced by two subcutaneous injections of AOM at 20 mg/kg given at the start of week 2 and week 3. Test article dosing then continued until the end of week 5.

The choice of dose level for balsalazide is made by review of other preclinical studies for efficacy in colitis models. A dose of 200 mg/kg/day in a 500 g rat equates to a dose of 14 g per day in a 70 kg human, approximately twice the therapeutic dose for treatment of active ulcerative colitis and over 4-fold the dose for maintaining remission. This dose level results in colonic concentrations of 5-ASA of 5–20 mM. The maximum tolerated dose of balsalazide in the rat is in excess of 12,000 mg/kg/day Body weights were recorded twice weekly, and water consumed by each cage of animals measured twice weekly. Consumption is calculated as average ml/animal/cage.

For aberrant crypt analysis, animals were sacrificed under $CO_2$ euthanasia at the end of either three weeks or five weeks of dosing. The large intestine was excised at the caecum and anus, removed and opened longitudinally. The tissue was freed from contents, rinsed in saline and fixed at 4° C. for two hour in 2% paraformaldehyde and stained with 0.2% methylene blue for 3–5 minutes. After a saline rinse, the number of foci of aberrant crypts was scored by counting under a microscope at 40–100X magnification. The length of the colonic tissue was also measured. A representative sample of the grossly identified lesions was embedded in glycol methacrylate at 4° C.; 3–4 μm sections of each foci are stained with hematoxylin, eosin and azure (HEA) for histological evaluation.

For gastroduodenal erosion analysis, the fundus, antrum, and duodenum were removed and processed separately as above. Gastric erosions were scored using the gastric erosion index of length and severity as described (Peskar et al. (1986) *Prostaglandins* 31:283–287).

Figure 4:
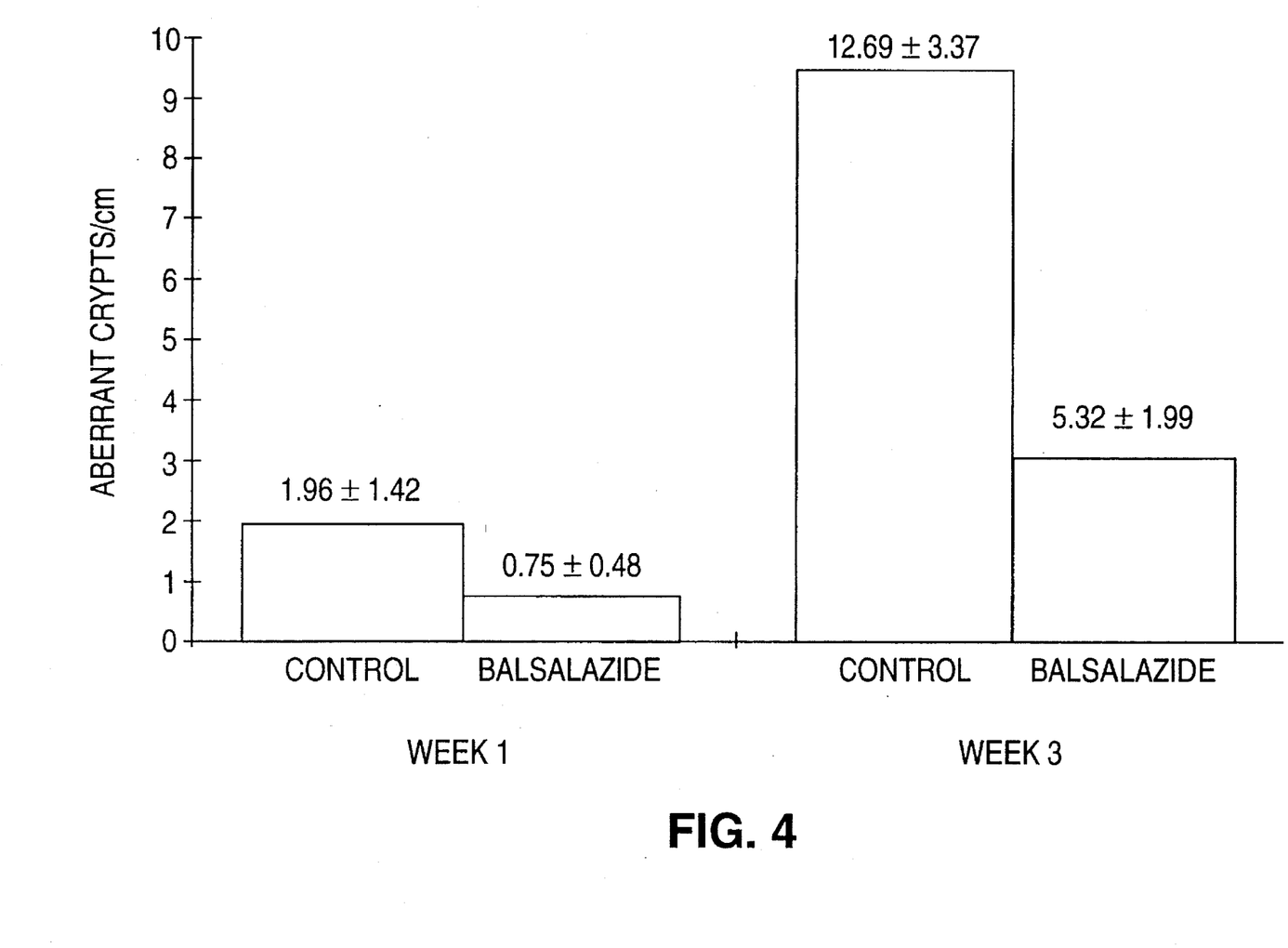
FIG. 4 shows an analysis of the number of aberrant colonic crypts induced by treating groups of rats with the carcinogen, azoxymethane in the presence and absence of balsalazide administered in the drinking water.

The results are shown in FIG. 4 where the average number of aberrant crypts per longitudinal cm of colonic tissue is shown for animals examined either one or three weeks following two subcutaneous injections of azoxymethane. At both time points the animals treated with balsalazide had a greatly reduced average number of aberrant crypts than the control animals. At week 1 there was a 61.8% inhibition and at week five there was a 58.1% inhibition in the average number of aberrant crypts All publications and patent applications cited in this specification are incorporated herein by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method of treating an individual suffering from colon cancer or at risk to develop colon cancer comprising administering to human in need thereof an effective amount of a pharmaceutical composition comprising a 2-hydroxy-5=phenylazobenzoic acid derivative of the general formula:

wherein X is an —$SO_2$— or —CO— group and R is either a phenyl or carboxymenthylphenyl radical or is a radical of the formula —(CH$_2$)$_n$—Y, in which Y is a hydroxyl group, an amino group, a monoalkyl- dialkyl-amino group, the alkyl moieties of which contain up to 6 carbon atoms, or a carboxylic or sulphonic acid group, and n is a whole number of from 1 to 6, and in which one or more of the hydrogen atoms in the alkylene radical can be replaced by amino groups, monoalkyl- or dialkyl-amino groups, the alkyl moieties of which contain up to 6 carbon atoms, or alkyl radicals, and in which the —(CH$_2$)$_n$—Y radical is either attached directly to the nitrogeno atom or via a benzene ring, with the proviso that R—NH—X— is other than a —CO—NH—CH$_2$—COOH radical; or an ester or its active metabolite 5-ASA, or a non-toxic, pharmacologically acceptable salt of the 2-hydroxy-5-phenylazobenzoic acid derivative or ester or its active metabolite 5-ASA.

2. A method according to claim 1 wherein the pharmaceutical composition consists essentially of the 2-hydroxy-5-phenylazobenzoic acid derivative or ester or its active metabolite 5-ASA or a salt of the 2-hydroxy-5-phenylazobenzoic acid derivative or an ester or its active metabolite 5-ASA in admixture with a solid or liquid pharmaceutical diluent or carrier.

3. A method according to claim 1 wherein the 2-hydroxy-5-phenylazobenzoic acid derivative is balsalazide.

4. A method of claim 1 wherein the pharmaceutical composition is administered orally to an individual suffering from or at risk to develop colon cancer in a daily dosage ranging from 1 to 14g per 70 kg body weight per day of the 2-hydroxy-5-phenylazobenzoic acid derivative or an ester or its active metabolite 5-ASA or a salt of the 2-hydroxy-5-phenylazobenzoic acid derivative or an ester or its active metabolite 5-ASA.

5. A method of claim 1 wherein the pharmaceutical composition is administered rectally to an individual suffering from or at risk to develop colon cancer in a daily dosage ranging from 1 to 14g per 70 kg body weight per day of the 2-hydroxy=5-phenylazobenzoic acid derivative or an ester or its active metabolite 5-ASA or a salt of the 2-hydroxy=5-phenylazobenzoic acid derivative or an ester or its active metabolite 5-ASA.

* * * * *